US008817076B2

(12) United States Patent
Steen

(10) Patent No.: US 8,817,076 B2
(45) Date of Patent: Aug. 26, 2014

(54) METHOD AND SYSTEM FOR CROPPING A 3-DIMENSIONAL MEDICAL DATASET

(75) Inventor: Erik N. Steen, Horten (NO)

(73) Assignee: General Electric Company, Schenectady, NY (US)

(*) Notice: Subject to any disclaimer, the term of this patent is extended or adjusted under 35 U.S.C. 154(b) by 561 days.

(21) Appl. No.: 13/197,223

(22) Filed: Aug. 3, 2011

(65) Prior Publication Data
US 2013/0033571 A1    Feb. 7, 2013

(51) Int. Cl.
*H04N 13/02* (2006.01)
*G06T 19/20* (2011.01)
*G09G 5/08* (2006.01)

(52) U.S. Cl.
CPC ......... *G06T 19/20* (2013.01); *G06T 2219/2016* (2013.01); *G06T 2210/22* (2013.01)
USPC .............................. 348/46; 345/158; 382/154

(58) Field of Classification Search
USPC ............................................ 348/46; 382/154
See application file for complete search history.

(56) References Cited

U.S. PATENT DOCUMENTS

| | | | |
|---|---|---|---|
| 6,059,727 A * | 5/2000 | Fowlkes et al. ............... | 600/443 |
| 6,175,610 B1 | 1/2001 | Peter | |
| 6,785,578 B2 | 8/2004 | Johnson et al. | |
| 7,834,847 B2 | 11/2010 | Boillot et al. | |
| 7,835,498 B2 * | 11/2010 | Bonfiglio et al. ............. | 378/115 |
| 7,840,040 B2 | 11/2010 | Wilcox et al. | |
| 7,894,663 B2 * | 2/2011 | Berg et al. ..................... | 382/154 |
| 8,139,110 B2 * | 3/2012 | Nishihara ...................... | 348/135 |
| 8,166,421 B2 * | 4/2012 | Magal et al. .................. | 715/863 |
| 8,180,114 B2 * | 5/2012 | Nishihara et al. ............. | 382/114 |
| 8,537,111 B2 * | 9/2013 | Underkoffler et al. ........ | 345/158 |
| 2005/0116957 A1 * | 6/2005 | Guang ............................ | 345/501 |
| 2007/0216642 A1 * | 9/2007 | Kneissler ....................... | 345/156 |
| 2009/0231278 A1 * | 9/2009 | St. Hilaire et al. ............ | 345/158 |
| 2010/0066676 A1 * | 3/2010 | Kramer et al. ................ | 345/158 |
| 2011/0103658 A1 * | 5/2011 | Davis et al. .................... | 382/128 |
| 2013/0063436 A1 * | 3/2013 | Li ................................... | 345/423 |

OTHER PUBLICATIONS

Kinect Sensor Allows Surgeons to Manipulate 3D CT Images in Midair, YouTube Video available at http://www.youtube.com/watch?v=id70ZAbFaVI, accessed Aug. 3, 2011, 2 pages.
Virtopsy—Potential use of gesture control in medicine using the Microsoft Kinect camera, YouTube Video available at http://www.youtube.com/watch?v=b6CT-YDChmE, accessed Aug. 3, 2011, 2 pages.

* cited by examiner

*Primary Examiner* — Sath V Perungavoor
*Assistant Examiner* — Howard D Brown, Jr.

(57) ABSTRACT

A method and gesture-based control system for manipulating a 3-dimensional medical dataset include translating a body part, detecting the translation of the body part with a camera system. The method and system include translating a crop plane in the 3-dimensional medical dataset based on the translating the body part. The method and system include cropping the 3-dimensional medical dataset at the location of the crop plane after translating the crop plane and displaying the cropped 3-dimensional medical dataset using volume rendering.

20 Claims, 5 Drawing Sheets

METHOD AND SYSTEM FOR CROPPING A 3-DIMENSIONAL MEDICAL DATASET

FIELD OF THE INVENTION

This disclosure relates generally to a gesture-based method of cropping a 3-dimensional medical dataset and a gesture-based control system for cropping a 3-dimensional medical dataset.

BACKGROUND OF THE INVENTION

When viewing a volume rendering of a 3-dimensional medical dataset it is frequently necessary for a user to crop the 3-dimensional medical dataset in order to more clearly view the desired anatomical structure. Cropping removes a portion of the 3-dimensional medical dataset in order to more clearly illustrate underlying structure. According to conventional techniques, a user must first select a crop plane to be adjusted and then control the positioning of the crop plane in order to crop only the unwanted portion of the image. A user would typically use a user interface device, such as a mouse or trackball, to first select the crop plane and then reposition the crop plane by dragging it with the user interface device. While effective, this conventional technique of cropping a 3-dimensional medical dataset is far from ideal, particularly in a sterile environment needed for surgery or other invasive medical procedures.

For example, if a surgeon is using the 3-dimensional medical dataset for reference during a surgical procedure, the user interface device must be kept sterile. The very nature of a user interface device like a mouse of trackball makes it difficult to keep sterile. For example, a mouse typically has multiple buttons and a trackball needs to spin freely within a keyboard or other mounting fixture. If covered in a sterile cover, the functionality of both devices may be somewhat compromised. It will also be necessary for staff to perform extra steps before each surgical procedure to ensure the sterility of the user interface device. Additionally, it is oftentimes awkward and inconvenient for the surgeon to transition from a workstation with the user interface device to the patient while performing a procedure.

Therefore, for these and other reasons, an improved method and control system for manipulating a 3-dimensional medical dataset is desired.

BRIEF DESCRIPTION OF THE INVENTION

The above-mentioned shortcomings, disadvantages and problems are addressed herein which will be understood by reading and understanding the following specification.

In an embodiment, a method of manipulating a 3-dimensional medical dataset includes translating a body part, detecting the translation of the body part with a camera system, and translating a crop plane in the 3-dimensional medical dataset based on the translation of the body part. The method includes cropping the 3-dimensional medical dataset at the location of the crop plane after translating the crop plane and displaying the cropped 3-dimensional medical dataset using volume rendering.

In another embodiment, a method of manipulating a 3-dimensional medical dataset includes performing an initialization gesture within a predetermined volume. The method includes detecting the initialization gesture with a camera system and determining with a processor the location of the initialization gesture within the predetermined volume. The method includes selecting with the processor one of a plurality of crop planes based on the location of the initialization gesture within the predetermined volume. The method includes performing a translation gesture within the predetermined volume and detecting the translation gesture with the camera system. The method includes determining with the processor a translation direction and a translation distance based on the translation gesture. The method includes moving the selected crop plane the translation distance in the translation direction. The method includes cropping the 3-dimensional medical dataset at the location of the crop plane after moving the crop plane and displaying the cropped 3-dimensional medical dataset as a volume rendering.

In another embodiment, a gesture-based control system includes a camera system, a display device connected to the camera system and a processor connected to the camera system and the display device. The processor is configured to display a volume rendering of a 3-dimensional medical dataset on the display device. The processor is configured to receive camera data of a translation gesture from the camera system. The processor is configured to segment a body part from the camera data. The processor is configured to determine a translation distance and a translation direction of the translation gesture from the camera data. The processor is configured to move the crop plane the translation distance in the translation direction. The processor is configured to crop the 3-dimensional medical dataset at the location of the crop plane and display the cropped 3-dimensional medical dataset on the display device using the volume rendering.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
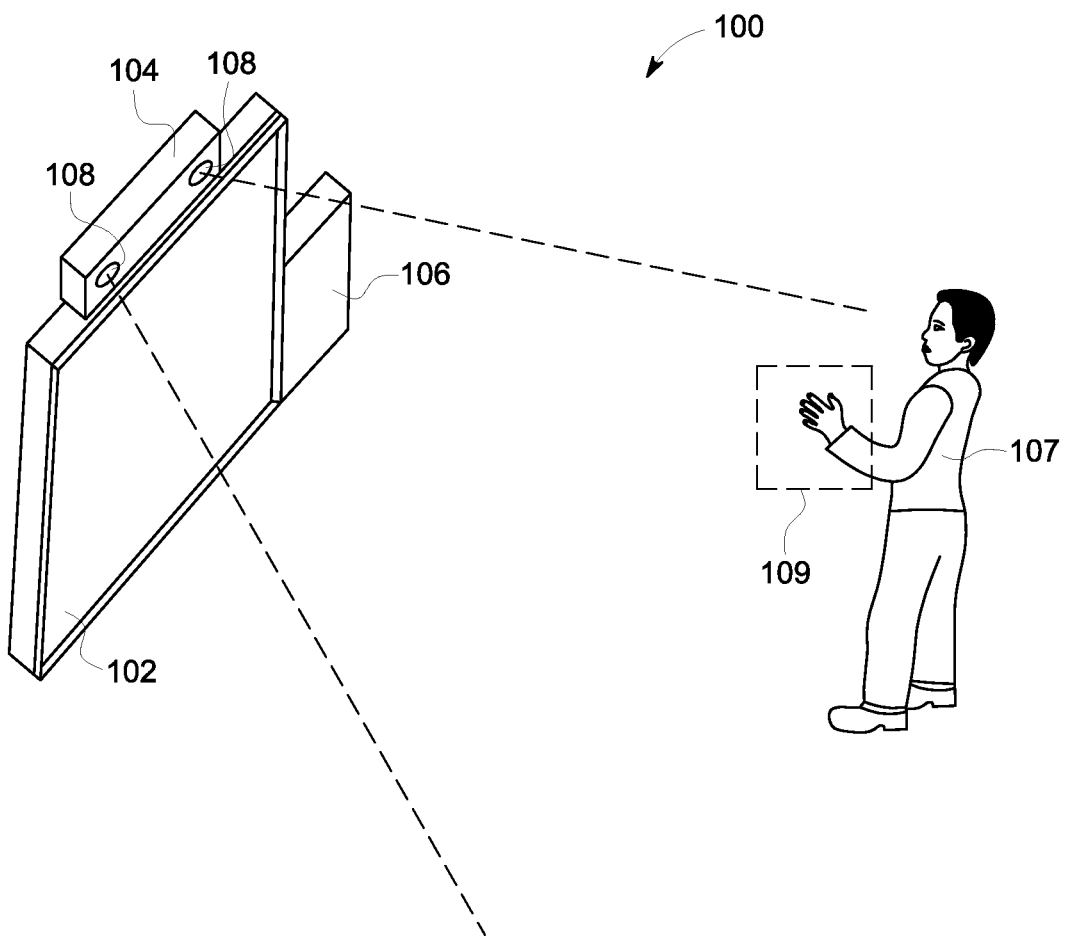
FIG. 1 is a schematic representation of a gesture-based control system in accordance with an embodiment.

FIG. 1 is a schematic representation of a gesture-based control system 100 in accordance with an embodiment. The gesture-based control system 100 includes a display device 102, a camera system 104, and a processor 106. A volume-rendered image may be displayed on the display device 102. According to an exemplary embodiment, the volume-rendered image may include an ultrasound image, such as a live ultrasound image that is updated in real-time as additional data is acquired. A user 107 is shown in a position detectable by the camera system 104 to further illustrate how the gesture-based control system 100 may be used. The user 107 may perform a gesture with a body part such as a hand 109. The camera system 104 includes two cameras 108 adjusted to detect camera data from an area in front of the display device 102. According to other embodiments, the camera system 104 may include just one camera. Additionally, the camera system may include two or more cameras in a different configuration according to other embodiments. For example, an embodiment may include a first camera positioned to record data from the display device 102 and a second camera positioned some distance in front of a plane defined by the display device 102. This configuration may be useful because the second camera can easily determine when the user 107 moves in a direction either towards the display device 102 or away from the display device 102.

A processor 106 receives a 3-dimensional medical dataset in accordance with an embodiment. The processor 106 crops the 3-dimensional medical dataset in accordance with gestures performed by the user 107. Additional details about how the processor crops the 3-dimensional medical dataset based on gestures will be described in additional detail hereinafter. The 3-dimensional medical dataset may include a 3-dimensional medical dataset from any 3-dimensional imaging modality, including computed tomography (CT), positron emission tomography (PET), X-ray, ultrasound, and the like. The gesture-based control system 100 may be integrated into a medical imaging system from any of the aforementioned modalities, the gesture-based control system 100 may be part of a workstation, or the gesture-based control system 100 may be a stand-alone system.

The processor 106 may use volume rendering to generate an image from the 3-dimensional medical dataset according to a number of different techniques. According to an exemplary embodiment, the processor 106 may generate a volume-rendered image through a ray-casting technique from a view plane (not shown). The processor 106 may cast a plurality of parallel rays from the view plane to the 3-dimentional medical dataset. Each voxel may be assigned a value and an opacity based on information in the 3-dimensional medical dataset. For example, starting at the front, that is the direction from which the image is viewed, each value along a ray may be multiplied with a corresponding opacity. The opacity weighted values are then accumulated in a front-to-back direction along each of the rays. This process is repeated for each of the pixels in the view plane in order to generate a volume-rendered image. In another embodiment an opacity value may be assigned to each sample and a volume composition may be performed according to a general rendering equation. According to an embodiment, the pixel values from the view plane may be displayed as the volume-rendered image. The volume-rendering algorithm may be configured to use an opacity function providing a gradual transition from opacities of zero (completely transparent) to 1.0 (completely opaque). The volume-rendering algorithm may factor the opacities of the voxels along each of the rays when assigning a value to each of the pixels in the view plane. For example, voxels with opacities close to 1.0 will block most of the contributions from voxels further along the ray, while voxels with opacities closer to zero will allow most of the contributions from voxels further along the ray. Additionally, when visualizing a surface, a thresholding operation may be performed where the opacities of voxels are reassigned based on the values. According to an exemplary thresholding operation, the opacities of voxels with values above the threshold may be set to 1.0 while voxels with the opacities of voxels with values below the threshold may be set to zero. This type of thresholding eliminates the contributions of any voxels other than the first voxel above the threshold along the ray. Other types of thresholding schemes may also be used. For example, an opacity function may be used where voxels that are clearly above the threshold are set to 1.0 (which is opaque) and voxels that are clearly below the threshold are set to zero (translucent). However, an opacity function may be used to assign opacities other than zero and 1.0 to the voxels with values that are close to the threshold. This "transition zone" is used to reduce artifacts that may occur when using a simple binary thresholding algorithm. A linear function mapping opacities to values may be used to assign opacities to voxels with values in the "transition zone". Other types of functions that progress from zero to 1.0 may be used in accordance with other embodiments.

In an exemplary embodiment, gradient shading may be used to generate a volume-rendered image in order to present the user with a better perception of depth regarding the surfaces. For example, surfaces within the 3-dimensional medical dataset may be defined partly through the use of a threshold that removes data below or above a threshold value. Next, gradients may be defined at the intersection of each ray and the surface. As described previously, a ray is traced from each of the pixels in the view plane to the surface defined in the 3-dimensional medical dataset. Once a gradient is calculated at each of the rays, the processor 106 (shown in FIG. 1) may compute light reflection at positions on the surface corresponding to each of the pixels and apply standard shading methods based on the gradients. According to another embodiment, the processor 106 identifies groups of connected voxels of similar intensities in order to define one or more surfaces from the 3D data. According to other embodiments, the rays may be cast from a single view point.

Figure 2:
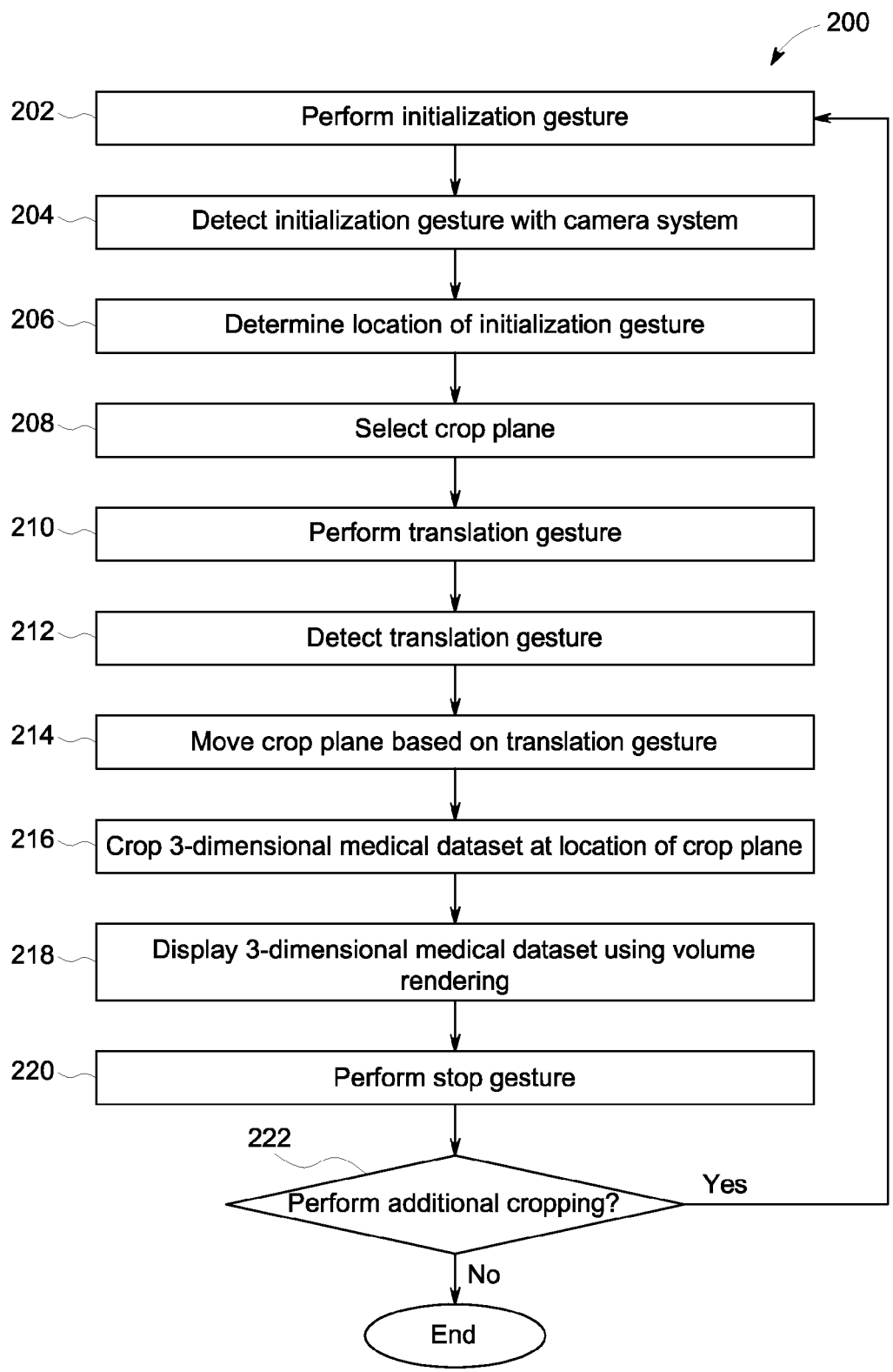
FIG. 2 is a flow chart of a method in accordance with an embodiment.

FIG. 2 is a flow chart of a method 200 of manipulating a 3-dimensional medical dataset in accordance with an embodiment. The individual blocks represent steps that may be formed in accordance with the method 200. The technical effect of the method 200 is the display of a cropped 3-dimensional medical dataset where the location of the cropping is determined based on a gesture.

Referring to both FIG. 1 and FIG. 2, at step 202, the user 107 performs an initialization gesture. The initialization gesture can be any gesture or movement that the combination of the camera system 104 and the processor 106 are able to detect. At step 204, the processor 106 detects the initialization gesture based on data from the camera system 104.

Figure 3:
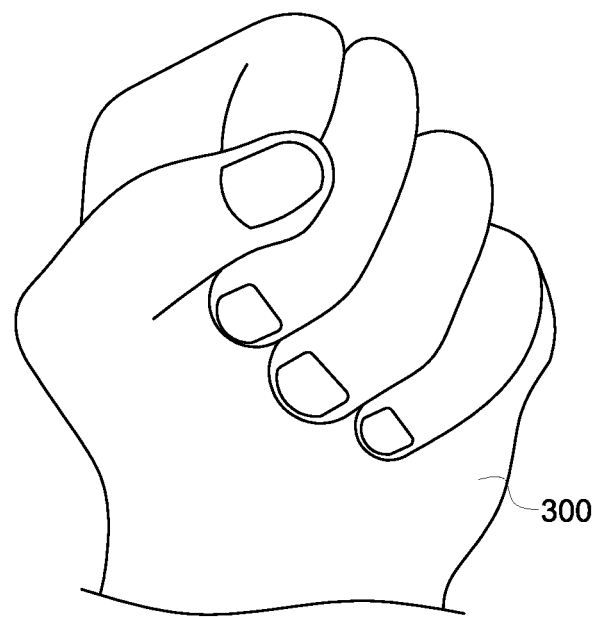
FIG. 3 is a schematic representation of a closed hand in accordance with an embodiment.
Figure 4:
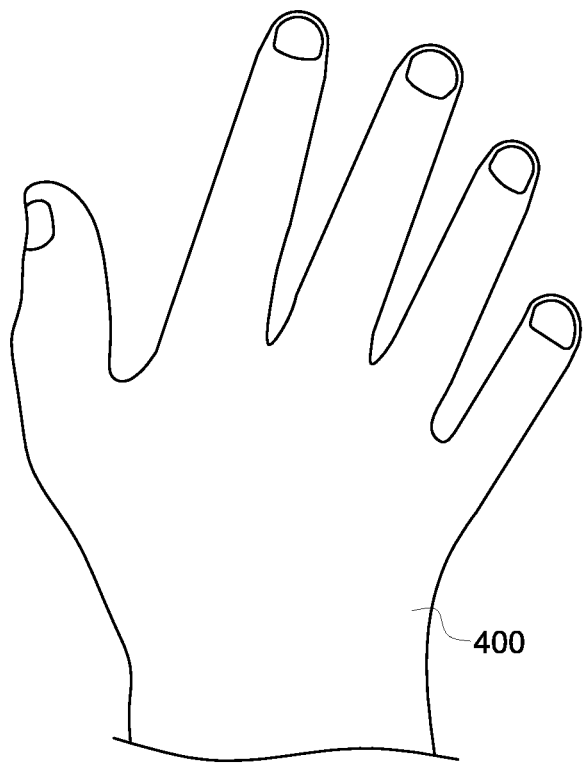
FIG. 4 is a schematic representation of an open hand in accordance with an embodiment.

FIG. 3 is a schematic representation of a closed hand in accordance with an embodiment and FIG. 4 is a schematic representation of an open hand in accordance with an embodiment. Referring now to FIGS. 1-4, according to an exemplary embodiment, at step 202, the user 107 may perform an initialization gesture of opening the user's hand 109 from a generally closed or fist-like position like that shown in the closed hand 300 of FIG. 3 to a generally open position like that shown in the open hand 400 of FIG. 4. The processor 106 may receive camera data from the camera system 104. An initial segmentation may be done in order to separate the operator's hand or body from the background. For example, the segmentation of the hand may be based on a combination of thresholding, color and motion cues to separate the hand from the background. The segmentation may furthermore isolates feature points from the hand and these feature points are used for motion tracking. The feature points can be mapped to a simplified model of a closed hand as well as an open hand. This is a exemplary way of performing image recognition in order to determine if the hand is open (corresponding to an operating mode according to an embodiment) or closed (corresponding to a non-operating mode according to an embodiment). Other segmentation techniques may also be used in accordance with other embodiments. The processor 106 may then search the relevant camera data for a shape consistent with an open hand 400 like that shown in FIG. 4. For example, the processor 106 may use an algorithm that searches for five appendages consistent with the user's open hand. Opening the user's hand is just one example of an initialization gesture and other initialization gestures may be used.

According to another embodiment, as part of a calibration step, the user 107 may be able to establish their own unique initialization gesture with the gesture-based control system 100. For example, the user may enter a calibration or set-up mode and then perform the desired initialization gesture within view of the camera system 104. Then the processor 106 would record this particular initialization gesture and search for this initialization gesture when manipulating a 3-dimensional medical dataset during a process such as the method 200. The processor 106 may use a combination of a shape-based detection algorithm and/or a movement detection algorithm in order to identify the initialization gesture.

Figure 5:
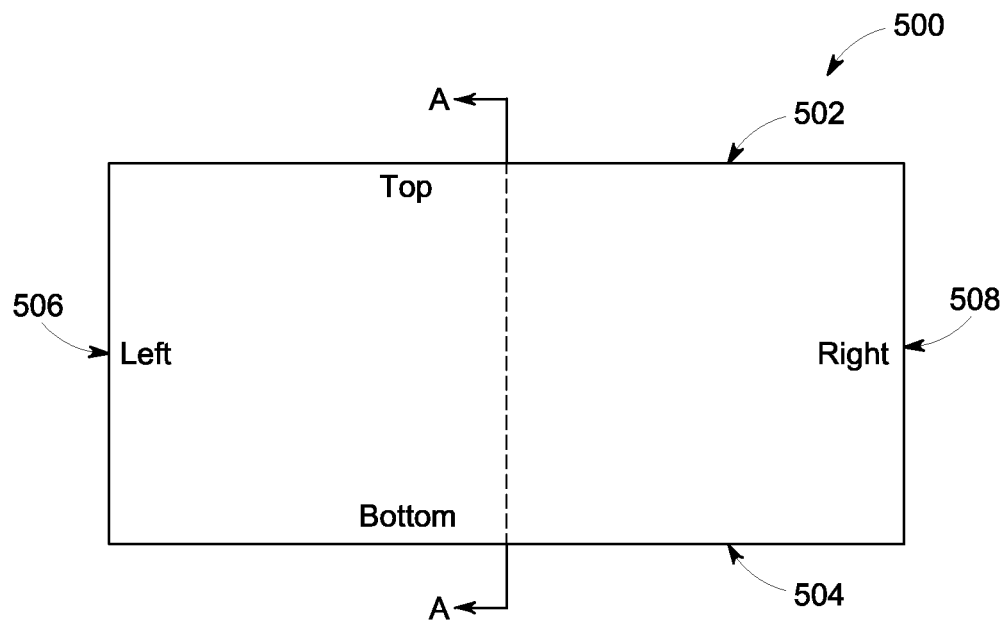
FIG. 5 is a schematic representation of a front elevational view of a box in accordance with an embodiment.
Figure 6:
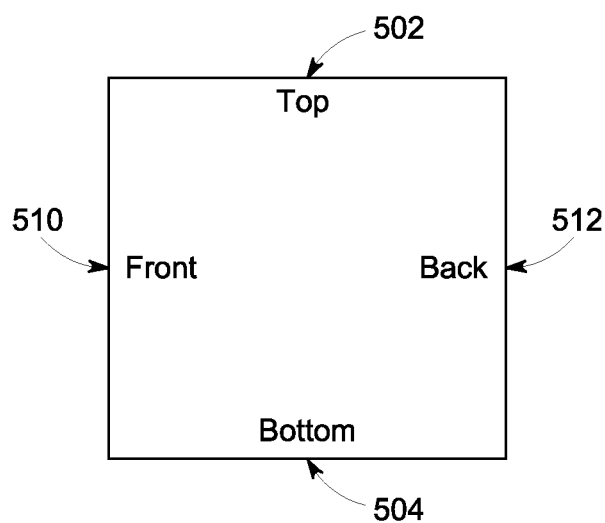
FIG. 6 is a schematic representation of a sectional view of a box in accordance with an embodiment.

FIG. 5 is a schematic representation of a front elevational view of a box 500 for cropping a 3-dimensional medical dataset in accordance with an embodiment. FIG. 6 is a schematic representation of a sectional view of the box 500 along sectional line A-A in accordance with an embodiment. Common reference numbers will be used to identify identical structures in both FIG. 5 and FIG. 6. Referring to both FIG. 5 and FIG. 6, the box 500 includes 6 sides: a top side 502, a bottom side 504, a left side 506, a right side 508, a front side 510, and a back side 512. Each of the sides defines a respective crop plane: the top side 502 defines a top crop plane; the bottom side 504 defines a bottom crop plane; the left side 506 defines a left crop plane; the right side 508 defines a right crop plane; the front side 510 defines a front crop plane; and the back side 512 defines a back crop plane. Additional details about the crop planes will be described hereinafter.

Figure 7:
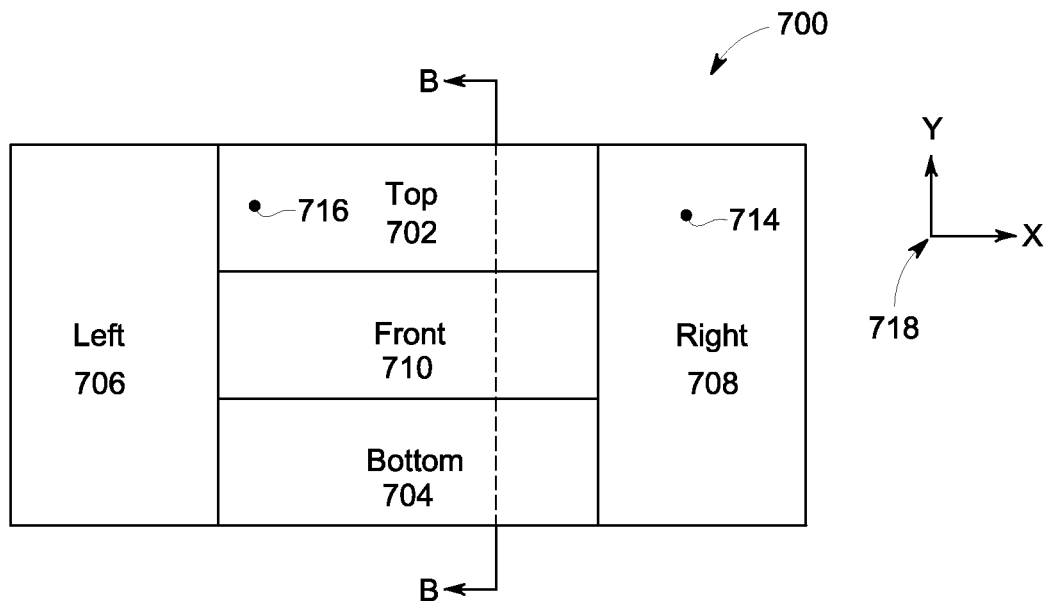
FIG. 7 a schematic representation of a front elevational view of predetermined volume in accordance with an embodiment.
Figure 8:
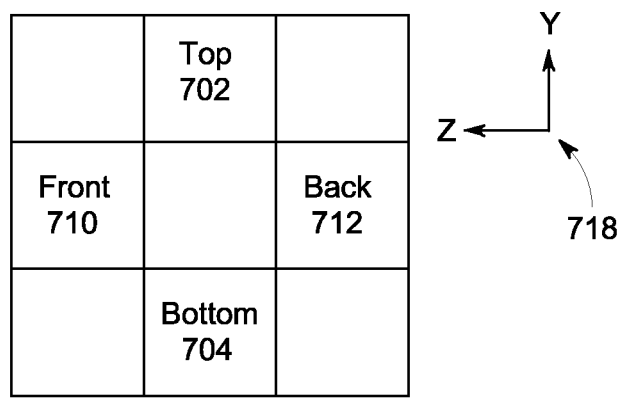
FIG. 8 is a schematic representation of a sectional view of a predetermined volume in accordance with an embodiment.

FIG. 7 is a schematic representation of a front elevational view of predetermined volume 700 defined with respect to the camera system 104 (shown in FIG. 1). FIG. 8 is a schematic representation of a sectional view of the predetermined volume 700 along sectional line B-B. The precise boundaries of the predetermined volume 700 may be determined by a user during a setup or calibration process or the predetermined volume 700 may be preset as a fixed size. According to an embodiment, the predetermined volume may be approximately 1 m wide, 0.5 m high and 0.5 m deep. Additionally, the predetermined volume 700 may be positioned approximately 3 m in front of the display device 102 (shown in FIG. 1) and approximately 1.5 meters above the floor. However, it should be understood that the predetermined volume 700 may be a different size and/or shape according to additional embodiments. Additionally, the predetermined volume 700 may be positioned in a different location with respect to the display device 102 in other embodiments.

Referring to both FIGS. 7 and 8, the predetermined volume 700 includes 6 sub-volumes according to an embodiment: a top sub-volume 702, a bottom sub-volume 704, a left sub-volume 706, a right sub-volume 708, a front sub-volume 710, and a back sub-volume 712. Referring additionally to FIG. 2, at step 206, the processor 106 (shown in FIG. 1) determines the location of the initialization gesture performed at step 202. According to an embodiment, the processor 106 uses input from the camera system 104 (shown in FIG. 1) to determine if the initialization gesture was performed in any of the 6 sub-volumes within the predetermined volume 700. The camera system 104 shown in FIG. 1 includes two cameras mounted on the display device 102. The cameras system 104 uses data from both of the cameras to more precisely define the 3D location where the initialization gesture was performed. Additionally, the camera system may use camera data including a focus depth of the cameras and/or the size of the body part used to perform the initialization gesture to accurately determine the location of the initialization gesture in a distance perpendicular to the display device 102. A coordinate axis 718 is shown with respect to FIGS. 7 and 8. The coordinate axis 718 shows an x-direction and a y-direction in FIG. 7 and a y-direction and a z-direction in FIG. 8. In accordance with an embodiment, the x-direction and the y-direction may be defined to be in planes parallel to the display device 102 (shown in FIG. 1). The z-direction may be defined in be a direction orthogonal to the display device 102.

At step 208 of FIG. 2, the processor 106 (shown in FIG. 1) selects a crop plane based on the location of the initialization gesture determined in step 206. According to an exemplary embodiment, the processor 106 may select the crop plane corresponding to the sub-volume where the initialization gesture is performed. For example, referring to FIGS. 5, 6, 7, and 8, if the initialization gesture is performed in the top sub-volume 702, then the processor 106 (shown in FIG. 1) selects the front crop plane. If the initialization gesture is performed in the bottom sub-volume 704, then the processor 106 selects the bottom crop plane. If the initialization gesture is performed in the front sub-volume 710, then the processor 106 selects the front crop plane. If the initialization gesture is performed in the back sub-volume 712, then the processor 106 selects the back crop plane. If the initialization gesture is performed in the left sub-volume 706, then the processor 106 selects the left crop plane. If the initialization gesture is performed in the right sub-volume 708, then the processor 106 selects the right crop plane.

At step 210, the user 107 (shown in FIG. 1) performs a translation gesture in a position that is detectable by the camera system 104 (shown in FIG. 1). According to the exemplary embodiment, the translation gesture may be a movement generally in one of three orthogonal directions: towards or away from the camera system 104 (i.e. in a z-direction); left or right with respect to the camera system 104 (i.e. in the x-direction); and up or down with respect to the camera system 104 (i.e. in the y-direction). The direction of the translation gesture should be compatible with crop plane selected at step 208. For example, the processor 106 may only allow the crop plane to be translated in a direction perpendicular to the surface of the crop plane. For example, the processor 106 would only allow the front crop plane to be translated in the z-direction. According to an embodiment, the translation gesture may include translating a body part, such as a hand, in the desired direction of translation. For example, the user may translate his hand to the left if moving either the left crop plane or the right crop plane to the left. Translation gestures may also include movements of a body part in other directions including directions including to the right, up, down, in towards the camera system 104, and out away from the camera system 104. According to an exemplary embodiment, crop planes will follow translation gestures to the left, right, up, down, in, and out. For translation gestures in a direction of either generally towards the camera system 104 or generally away from the camera system 104, the processor 106 may adjust either the front crop plane or the back crop plane in the direction corresponding either into the image or out from the image. By first identifying a crop plane, and determining reasonable translation directions for that crop plane, the user is not required to make as precise of a translation gesture. That is, since, according to an embodiment, the processor 106 will only allow the crop planes to be translated in a direction perpendicular to the plane, if the user makes a gesture that is generally in the correct direction, the processor 106 will move the crop plane accordingly.

At step 212, the processor 106 detects the translation gesture. After detecting the initialization gesture at step 204, the processor 106 is configured to detect the translational motion of a body part. According to an embodiment where the opening of a hand is used as the initialization gesture, the processor 106 may be configured to segment the user's hand based on data from the camera system 104 and then track the movement of the user's hand over time. In one such embodiment, the processor 106 may identify an object with multiple projections spatially positioned in a manner consistent with fingers of a hand. Other object recognition techniques may be used to identify the user's body part while performing the translation gesture.

At step 214, the processor 106 moves the crop plane based on the user's translation gesture. For example, the processor 106 may determine a translation direction and a translation distance based on the translation gesture. For example, the processor 106 may determine the direction of the translation gesture based on the data from the camera system 104 and then the processor 106 may determine a translation distance based on the distance the user's body part is moved during the translation gesture. According to an embodiment, the translation gesture may be performed within the predetermined volume 700 (shown in FIG. 7). The translation distance may be calculated based on the distance covered by the translation gesture within the predetermined volume 700. Additionally, a scaling factor may be applied to determine the translation distance based as a percentage of the distance covered by the translation gesture within the predetermined volume 700.

At step 216, the processor 106 crops the 3-dimensional medical dataset at the location of the crop plane that was moved during step 214. The cropping of a 3-dimensional medical dataset may be performed in several ways. In one embodiment cropping may be performed by removing data from the 3-dimensional medical dataset. In another embodiment cropping may be performed by simply excluding samples that are outside the cropping planes during ray casting. In yet another embodiment, a graphics card with hardware support for clipping planes may be used to perform the cropping during the volume rendering process. Still referring to FIG. 2, at step 218 the processor 106 (shown in FIG. 1) displays the cropped 3-dimensional medical dataset on the display device 102 (shown in FIG. 1) using volume rendering. According to an embodiment, the cropping of the 3-dimensional medical dataset at step 216 and the displaying a volume rendering of the cropped 3-dimensional medical dataset at step 218 may be performed in real-time with the performing of the translation gesture at step 210. That is, as the user performs the translation gesture, the volume rendering displayed on the display device 102 may be updated in real-time to reflect the repositioning of the crop plane while the user is in the process of performing the translation gesture. This is advantageous because it allows the user to see the results of the modification to the location of the crop plane before completing the cropping process. Additionally, if the user moves the crop plane too far and prefers the crop plane to be in an intermediate position, the user may simply adjust the translation gesture.

The user may indicate that the translation gesture is complete by performing a stop gesture, as indicated at step 220. According to an embodiment where the opening of the hand is used as the initialization gesture, the stop gesture may include closing the hand. Other embodiments may use different stop gestures. At step 222, the user decides if he would like to perform any additional image cropping. If the user would like to either make a further adjustment to the crop plane that was previously adjusted or adjust any of the other crop planes, then the method 200 returns to step 202. If it is not desired to make any additional adjustments to the crop planes, then the method 200 ends.

While the method 200 was described as a series of discrete steps, it should be appreciated that the process of cropping a 3-dimensional medical dataset according to the method 200 may be performed in a fluid and continuous manner by a user. An exemplary crop plane adjustment performed by using the method 200 will be described to further illustrate how the method 200 may benefit a user. By using the method 200, the user is able to quickly and accurately crop a 3-dimensional medical dataset by adjusting one or more crop planes. For example, referring to FIG. 2 and FIG. 7, the user may open his hand at point 714 in the predetermined volume 700. The opening of his hand is an initialization gesture recognized by the processor 106 and, based on the location of the initialization gesture in the right sub-volume, the right crop plane is selected. The user may than translate his open hand from point 714 to point 716. This translation gesture is recognized by the processor and the right crop plane is translated. The distance from point 714 to point 716 within the predetermined volume is calculated by the processor 106 and, if necessary, a scaling factor is applied to the distance in order for the processor to calculate the distance that the right crop plane should be moved with respect to the volume rendering of the 3-dimensional medical dataset shown on the display device 102. The right crop plane may be moved in real-time as the user translates his open hand. The processor crops the 3-dimensional medical dataset at a position corresponding to point 716 and the cropped image is displayed on the display device 102. The user may close his hand at point 716 in the predetermined volume 700. The closing of the hand is a stop gesture detected by the processor 106. The stop gesture indicates that the adjustment to the right crop plane is finished unless the user decides to make a further adjustment to the right crop plane by repeating the method 200 an additional time. The processor 106 may deselect the crop plane in response to the stop gesture. Thus, by simply opening his hand and translating his hand, the user is able to quickly select the desired crop plane and crop the 3-dimensional medical dataset. By performing the method 200 multiple times, that is adjusting multiple crop planes through the steps of the method 200, the user is able to quickly adjust the 3-dimensional medical dataset in order to display the most critical anatomy without any concerns about the sterility of user interface. Additionally, the user gains a significant time advantage if he is in the process of a surgical procedure because he does not need to step away from the procedure to crop the 3-dimensional medical dataset.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of manipulating a 3-dimensional medical dataset comprising:
   translating a body part;
   receiving camera data of said translating the body part from a camera system;
   determining with a processor a translation distance and a translation direction from the camera data based on at least one of feature tracking and a focus depth of the camera system;
   translating a crop plane in the 3-dimensional medical dataset based on the translation distance and the translation direction;
   cropping the 3-dimensional medical dataset at the location of the crop plane after said translating the crop plane; and
   displaying the cropped 3-dimensional medical dataset using volume rendering.

2. The method of claim 1, wherein said translating the body part comprises translating a hand.

3. The method of claim 1, wherein said cropping the 3-dimensional medical dataset comprises removing a portion of the image to one side of the crop plane.

4. The method of claim 3, wherein the cropped 3-dimensional medical dataset comprises a live ultrasound image.

5. The method of claim 1, wherein said translating the crop plane occurs in real-time while said translating the body part.

6. The method of claim 1, further comprising implementing a segmentation algorithm to identify the body part.

7. A method of manipulating a 3-dimensional medical dataset comprising:
   performing an initialization gesture within a predetermined volume;
   detecting the initialization gesture with a camera system;
   determining with a processor the location of the initialization gesture within the predetermined volume;
   selecting with the processor one of a plurality of crop planes based on the location of the initialization gesture within the predetermined volume, wherein the crop plane comprises one of six planes oriented in a box;
   performing a translation gesture within the predetermined volume;
   detecting the translation gesture with the camera system;
   determining with the processor a translation direction and a translation distance based on the translation gesture;
   moving the selected crop plane the translation distance in the translation direction;
   cropping a 3-dimensional medical dataset at the location of the crop plane after said moving the crop plane; and
   displaying the cropped 3-dimensional medical dataset using volume rendering.

8. The method of claim 7, wherein the initialization gesture comprises opening a hand.

9. The method of claim 8, wherein the translation gesture comprises translating the hand.

10. The method of claim 7, wherein the initialization gesture comprises closing a hand.

11. The method of claim 10, wherein the translation gesture comprises translating the hand.

12. The method of claim 7, further comprising performing a stop gesture after said performing the translation gesture.

13. The method of claim 12, further comprising detecting the stop gesture and deselecting the crop plane.

14. The method of claim 7, wherein said moving the selected crop plane the translation distance in the translation direction occurs in real-time while said performing the translation gesture.

15. A gesture-based control system comprising:
   a camera system;
   a display device connected to the camera system; and
   a processor connected to the camera system and the display device, wherein the processor is configured to:
      display a volume rendering of a 3-dimensional medical dataset on the display device;
      receive camera data of a translation gesture from the camera system;
      segment a body part from the camera data;
      determine a translation distance and a translation direction of the translation gesture from the camera data based on feature tracking;
      move the crop plane the translation distance in the translation direction;
      crop the 3-dimensional medical dataset at the location of the crop plane; and
      display the cropped 3-dimensional medical dataset on the display device using volume rendering.

16. The gesture-based control system of claim 15, wherein the camera system comprises a single camera.

17. The gesture-based control system of claim 15, wherein the camera system comprises multiple cameras.

18. A gesture-based control system comprising:
   a camera system;
   a display device connected to the camera system; and
   a processor connected to the camera system and the display device, wherein the processor is configured to:
      display a volume rendering of a 3-dimensional medical dataset on the display device;
      receive camera data of a translation gesture from the camera system;
      segment a body part from the camera data;
      determine a translation distance and a translation direction of the translation gesture from the camera data based on a focus depth of the camera system;
      move the crop plane the translation distance in the translation direction;
      crop the 3-dimensional medical dataset at the location of the crop plane; and
      display the cropped 3-dimensional medical dataset on the display device using volume rendering.

19. The gesture-based control system of claim 18, wherein the camera system comprises of a single camera.

20. The gesture-based control system of claim 18, wherein the camera system comprises multiple camera.

* * * * *